United States Patent

Flomenblit et al.

[11] Patent Number: 5,562,641
[45] Date of Patent: Oct. 8, 1996

[54] TWO WAY SHAPE MEMORY ALLOY MEDICAL STENT

[75] Inventors: Josef Flomenblit; Nathaly Budigina, both of Holon; Yuval Bromberg, Ramat-Hasharon, all of Israel

[73] Assignee: A Bromberg & Co. Ltd., Tel-Aviv, Israel

[21] Appl. No.: 246,823

[22] Filed: May 20, 1994

[30] Foreign Application Priority Data

May 28, 1993 [IL] Israel ........................................ 105828

[51] Int. Cl.$^6$ .................................................. A61M 25/00
[52] U.S. Cl. .......................... 604/281; 604/104; 606/198; 623/1; 623/11
[58] Field of Search ..................................... 604/281, 104, 604/890.1; 606/191, 198, 108; 623/1, 11, 900

[56] References Cited

U.S. PATENT DOCUMENTS

| | | | |
|---|---|---|---|
| 4,170,990 | 10/1979 | Baumgart et al. | 606/62 |
| 4,795,458 | 1/1989 | Regon | 606/191 |
| 4,984,581 | 1/1991 | Stice | 604/95 |
| 5,037,427 | 8/1991 | Harada et al. | 604/96 |
| 5,078,684 | 1/1992 | Yasuda | 604/281 |
| 5,089,005 | 2/1992 | Harada | 604/104 |
| 5,201,901 | 4/1993 | Harada et al. | 606/198 |

*Primary Examiner*—Corrine M. McDermott
*Assistant Examiner*—N. Kent Gring
*Attorney, Agent, or Firm*—Fitch, Even, Tabin & Flannery

[57] ABSTRACT

A stent for placing in a tubular organ so as to support its diameter to remain above a critical diameter. The stent comprises a spiral coil or cylinder made of a two-way shape memory alloy and has a super-elastic state in which the stent's diameter is at least about the critical diameter or more but within a physiological range tolerated by the organ and having a soft state in which the stent's diameter, after changing to this state from the super-elastic state, which is less than the critical diameter. The shape memory alloy has two transition temperatures being within a range that will not damage biological tissue, of which a first transition temperature is a temperature in which it changes from the soft state to the super-elastic state and of which a second transition temperature is a temperature in which it changes from the super-elastic state to the soft state. The arrangement being such that after changing into one of the two states, the stent remains in that state at body temperature.

11 Claims, 4 Drawing Sheets

TWO WAY SHAPE MEMORY ALLOY MEDICAL STENT

FIELD OF THE INVENTION

The present invention provides stents intended for placing inside tubular organs so as to prevent narrowing of the organ's diameter below a certain critical diameter. More specifically, the present invention provides stents made of two-way shape memory alloy.

The present invention further provides a catheter device for deploying or removing the stents.

BACKGROUND OF THE INVENTION

In many clinical situations it is necessary to ensure that a tubular organ will retain a diameter above a certain critical diameter. Such is the case, for example, where a coronary artery is expanded with an angioplasty catheter, in which case it is desired to prevent the expanded portion from being narrowed again. Another example is in the case of tracheal cancer, in which it is necessary to ensure that the trachea remains open in order to avoid suffocation.

Stents prepared by weaving a stainless steel wire in the form of a net has been proposed (*Surgery*, 1986, 99, 199–205). Another stent formed of a one-way shape memory allow was proposed in Japanese Published Application No. 61-6655. Such stents are introduced into a predetermined location in the tubular organ and then allowed to expand. However, such stents after once put in position are fixed and cannot be removed. This is a serious drawback in cases where the stent has to be removed or when the initial position of the stent is inaccurate and has to be improved. In all such cases, removal of the stent can cause serious injury to the tubular organ.

U.S. Pat. No. 5,037,427, discloses a stent made of a two-way shape memory alloy and means for its deployment in and recovery from a tubular organ. In accordance with this patent, the stent has a transition temperature which is below the body temperature in which it changes its diameter from a narrow diameter to a wide diameter in which it attaches to the walls of the tubular organ. The stent is inserted into the tubular organ under a constant flow of cold fluid and once the correct position of stent is reached, the flow of the cold fluid is stopped and the stent then expends under the influence of the body temperature. For removal, the stent is cooled again and withdrawn under a continuous application of a cold fluid. It will no doubt be appreciated that a continuous application of a cold fluid may not always be practical, and this is a continuous drawback for various applications.

It is the object of the present invention to provide a novel stent.

It is furthermore the object of the present invention to provide a stent which can easily be deployed and removed in a tubular organ.

It is furthermore the object in accordance with a preferred embodiment of the present invention to provide a stent which provides a constant pressure on the walls of a tubular organ.

It is still a further object of the present invention to provide means adapted for deployment and removal of the stent into and from a tubular organ.

The remaining object of the present invention will be realized from the following description.

GENERAL DESCRIPTION OF THE INVENTION

The present invention provides a stent for placing in a tubular organ so as to support its diameter to remain above a critical diameter, the stent comprising:

a spiral coil or cylinder made of a two-way shape memory alloy; having a super-elastic state in which the stent's diameter is at least about said critical diameter or more but within a physiological range tolerated by said organ and having a soft state in which the stent's diameter, after changing to this state from the super-elastic state, which is less than said critical diameter;

the shape memory alloy has two transition temperatures being within a range that will not damage biological tissue, of which a first transition temperature is a temperature in which it changes from said soft state to said super-elastic state and of which a second transition temperature is a temperature in which it changes from said super-elastic state to said soft state; whereby after changing into one of the two states, the stent remains in that state at body temperature.

The present invention further provides a catheter device adapted for deployment of the stent in a tubular organ.

The catheter device of the present invention is preferably adapted also for removal of the stent from the tubular organ or altering its position within the organ.

The invention will now be illustrated with reference to some non-limiting specific embodiments depicted in the annexed drawings.

DESCRIPTION OF SPECIFIC EMBODIMENTS

The stent of the present invention can be made of a wide variety of a two-way shape memory alloy such as Ni-Ti binary alloy, known as "nitinol", Ni-Ti-X (X being V, Co, Cu, Fe) ternary alloy, Cu-Al-Ni ternary alloy, or Cu-Zn-Al ternary alloy. A two-way shape memory alloy can be conditioned to have two different distinct shapes in its two states, the first state and the second state as referred to above.

A two-way shape memory alloy of the kind used in accordance with the invention has two transition temperatures: a first transition temperature being above body temperature in which it changes from its soft state into its super-elastic state, and a second temperature, being below body temperature, in which it changes from the super-elastic state into the soft state. In the super-elastic state, the shape memory alloy has super-elastic properties, namely, the pressure that the stent exerts on the surrounding tubular organ is constant within a certain range independent on the tubular organ's diameter. Owing to these properties, the stent can adapt itself, within a certain range, to the diameter of the tubular organ in which it is contained. The super elasticity properties depend also on the stent's shape, and owing to the elasticity inherent in the structure, a stent having the shape of a spiraled coil is preferred in accordance with the invention for most applications. A spiraled coil stent has a wider diameter range in which it retains its super elasticity and thus can better accommodate itself to the tubular organ in which it is contained, as will be elucidated further below. However, stents of other shapes, e.g. cylindrical, can also at times be employed in accordance with the invention.

The stent in accordance with the present invention is conditioned to have a diameter in which it supports the walls of the tubular organ in which it is contained in the super-elastic state, and a narrow diameter in the soft state.

Figure 1:
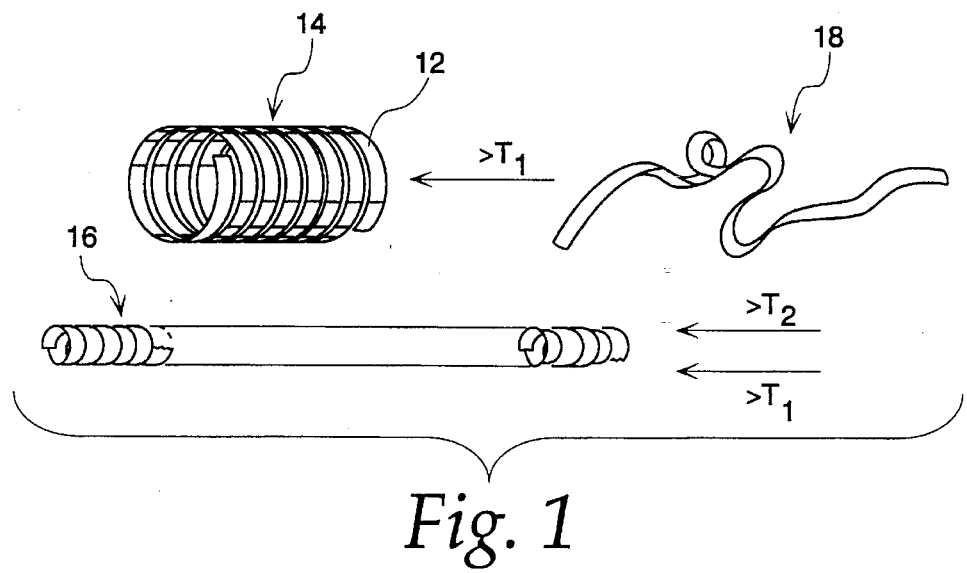
FIG. 1 shows the behavior of a stent in accordance with the invention upon change in temperature.

Reference is now being made to FIG. 1 showing various configurations of a stent in accordance with the invention. The stent which consists of a band 12 made of a two-way shape memory alloy, is conditioned in said super-elastic state to have the shape of a spiral coil 14 of a diameter which is about that of the tubular organ. In its soft state the stent is conditioned to have the shape of a spiral coil 16 having a narrower diameter than that it has in its super-elastic state. In said soft state, band 12 is relatively soft and may easily be formed into any desired form, such as the random form 18, or be tightly coiled on a catheter, etc.

When the temperature of the band is increased above $T_1$, the first transition temperature, the band immediately changes into the form 14 it has in its super-elastic state and when the temperature is reduced below $T_2$, the second transition temperature, the diameter of the stent narrows as it assumes its form 16 in said soft state.

In accordance with the present invention, the first transition temperature $T_1$ is typically within the range of 40°–80° C., while the second temperature is typically within the range of −10°–+20° C.

Prior to insertion into a tubular organ, the stent is in its soft state in which it is coiled tightly onto a catheter. Once the catheter is brought into proper position inside the tubular organ, the stent is heated by means such as those described below, whereupon its diameter increases to its super-elastic state and the stent thus presses on the walls of the tubular organ. In order to remove the stent, the catheter is inserted back into the tubular organ through the stent, the stent is cooled by means such as those described below, whereby the stent shrinks to its soft state. In this state, the stent either recoils onto the catheter or, alternatively, owing to its super softness in this state, the stent may simply be pulled out without causing any tissue damage. Typically, the stent is 5–10 times softer in the soft state than in the super-elastic state.

Figure 2:
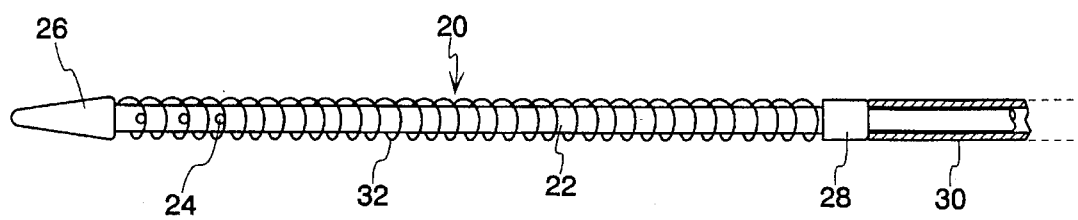
FIG. 2 is a schematic representation of a stent in accordance with one embodiment of the invention, tightly coiled on a catheter device, prior to its insertion into the tubular organ.

Attention is now being made to FIG. 2 showing a stent and a catheter device in accordance with one embodiment of the present invention. The catheter device 20 consists of a tubular duct 22 having a set of nozzles 24 at its front end. Device 20 further has a guiding member 26 at its front end having a base which is of a larger diameter than catheter 20, and further has an annular member 28 and an associated tube 30. Annular member 28 fits snugly on duct 22 but can nevertheless slide on duct 22 if forced by a relative movement of duct 22 and tube 30.

Stent 32 in its soft state, is coiled around duct 22 and is retained from sliding longitudinally on catheter 20 by the base of guide member 26 and by annular member 28. Stent 32 may be a continuous helical coil, or may consist of several discrete coils, the latter being at times advantageous in deployment of the stent within the tubular organ as may be realized from the following description.

Figure 3A:
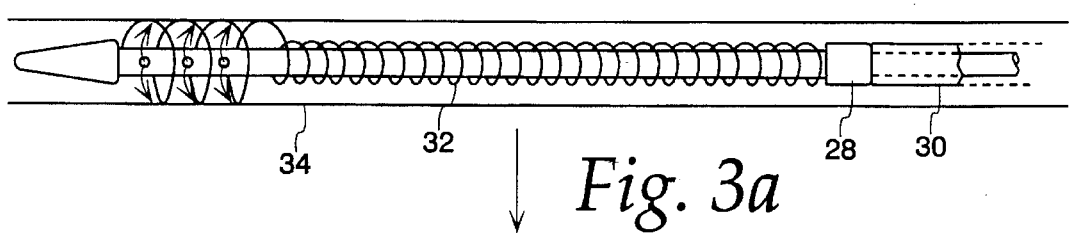
FIG. 3 depicts the sequence of deployment of the stent of FIG. 2 in a tubular organ.
Figure 3B:
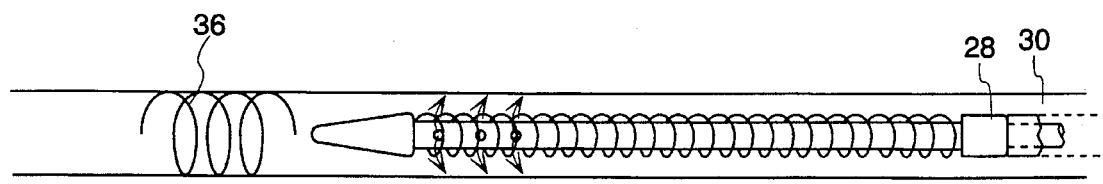
Figure 3C:

Reference is now being made to FIG. 3 showing the sequence of deployment of the stent of FIG. 2 in the tubular organ. Device 20 with coiled stent 32 is inserted into position inside tubular organ 34 (FIG. 3a), warm fluid (e.g. 50°–80° C.) is then injected through duct 22 and exits through nozzles 24. The warm fluid may be warm saline in case the tubular organ is for example a blood vessel or the ureter, or may be warm gas in case the tubular organ is for example a trachea. Upon ejection of the warm fluid, the segment of the stent which comes into contact with the warm fluid expands to its super-elastic state. As can be seen in FIGS. 3b and 3c, after deployment of the first of coils 36 duct 20 is pulled and tube 30 which remains stationary arrests the rearward movement of annular member 28 which in turn holds the stent 32 whereby the next coil of the stent becomes positioned over nozzles 24. By repeating this sequence all coils 34 of the stent 32 are deployed as shown in FIG. 3c.

The advantage of having the stent consisting of several discrete coils rather than one continuous coil is clearly apparent from FIG. 3. During expansion, the stent decreases in length and should the stent consist of one continuous coil, this would give rise to longitudinal movement thereof inside the tubular organ, which movements are undesired as they may inflict damage on the surrounding tissue. Additionally, as can be seen in FIGS. 3b and 3c, the fact that the stent consists of several discrete members may allow to deploy it over a longer length of the tubular organ. This may be of importance, for example, in cases of inaccurate initial placement of the device inside the tubular organ.

It should be pointed out that another way to avoid such longitudinal movement, is to increase the number of windings of the stent per unit length in its soft state so that the total stent length in the two states will be the same. The number of windings per unit length may be considerably increased if the band is wound several times on itself at each point.

For removal of the stent or for changing its position, a reverse sequence of operation to that described in FIG. 3 is performed. The device is inserted into the tubular organ to the position of the stent and then upon ejection of a cool liquid through the nozzles, the stent shrinks onto the catheter.

In addition to using a hot fluid, the expansion may also be achieved by other means such as by passing an electric current through stent or the use of radio frequency (RF) electromagnetic irradiation.

Reference is now being made to FIG. 4 showing an embodiment in accordance with the invention in which the heating of the stent is performed by passing an electric current therethrough. The catheter device in accordance with this embodiment generally designated 40, depicted in its initial state in FIG. 4a, comprises a flexible tube 42 and a flexible rod 44 contained therein. Rod 44 contains within it two electric wires 46 and 48 connected to an electric power source (not shown) and ending in terminals 50 and 52, adapted to receive the two ends of stent 54 coiled on the terminal segment of rod 44. Once the device is brought into position inside the tubular organ in this case in front of a constricted portion of the tubular organ, rod 44 is pushed out of tube 42, as shown in FIG. 4b, and then current is applied between wires 46 and 48, whereby the current flowing through stent 54 heats it up and causes its expansion and deployment in the tubular organ as shown in FIG. 4c, pressing on the walls of the tubular organ and causes them to expand.

Figure 4A:
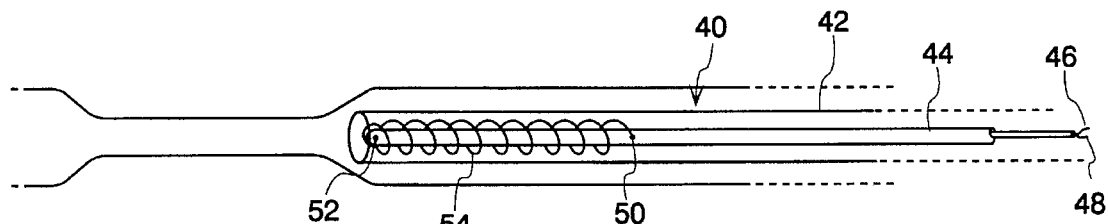
FIG. 4 depicts the deployment of a stent in accordance with another embodiment of the invention in which the expansion of the stent is induced by passing an electric current through the stent.
Figure 4B:
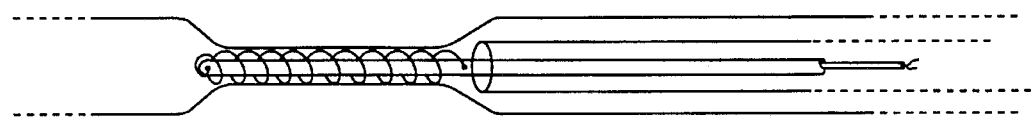
Figure 4C:
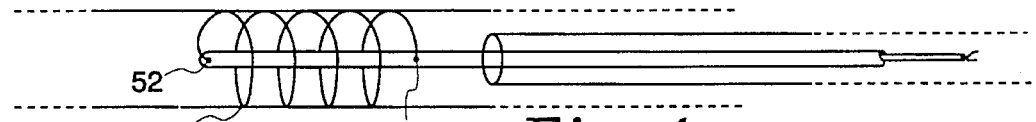
Figure 4D:
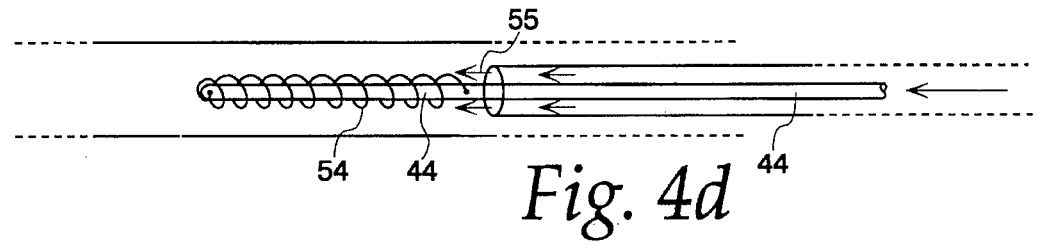

Terminals 50 and 52 are adapted for detachment from the two ends of stent 54, by pulling of rod 44, but until such time in which rod 44 is pulled, stent 54 still remains connected to terminals 50 and 52, as can be seen in FIG. 4c. If the positioning of the stent was inaccurate, it can be caused to shrink by the ejection of a cool fluid, represented by arrows 55 in FIG. 4d and can then be repositioned.

In order to remove the stent, device 40 is inserted back into the tubular organ, rod 44 pushed through stent 54 and then cool fluid, is ejected out of tube 42 causes the stent to shrink onto rod 44 and the rod with the stent can then be retracted back into tube 42 and removed.

Figure 5:
FIG. 5 depicts a stent and a device in accordance with another embodiment of the invention in which the expansion of the stent is controlled by a radio frequency (RF) antenna inside the catheter.

Attention is now being made to FIG. 5 showing another embodiment of the invention. The device in accordance with this embodiment operates in a similar manner to that of FIG. 4, the difference being that rather than expanding the stent by passing electric current therethrough, the stent in accordance with this embodiment is heated by the use of RF electromagnetic radiation. Similarly as in the embodiment of FIG. 4, flexible tube 56 contains a flexible rod 58. Rod 58 contains within it a lead 60 which is connected to an RF source (not shown) and linked at its front end to an RF antenna 62. Stent 54 is held on rod 58 at its portion containing antenna 62. An RF irradiation, e.g. in the microwave range, heats up the stent and causes its expansion. The RF antenna 62 in the embodiment depicted in FIG. 5 has the same length as the stent, but in some embodiments, in order to allow a measure of control of the stent's expansion, similarly as in the embodiment of FIG. 2, the RF antenna may be confined to only the front portion of rod 58, and then the stent can be controllably deployed by retracting rod 58 in a similar manner as performed in the embodiment of FIG. 2.

In addition to heating the stent by RF irradiation in the manner shown in FIG. 5, the RF irradiation may also be applied from an external source, e.g. by the use of a wide variety of instruments which are routinely used for remote heating of organs or tissues.

Figure 6A:
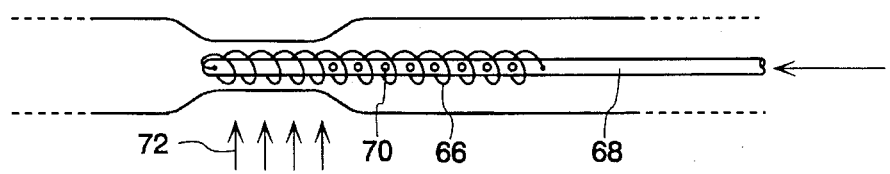
FIG. 6 depicts the deployment of a stent using external RF irradiation.
Figure 6B:
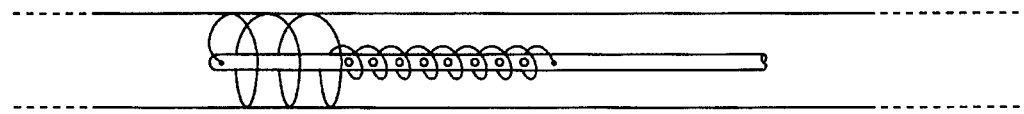

Reference is now made to FIG. 6 showing the heating of a stent by the use of an external RF irradiation source. In order to control the expansion of stent 66, member 68 on which the stent is held is a hollow tube having nozzles 70 extending through a region spanning almost the entire length of the stent but for a small front portion of the stent. Prior to the switching on of the RF source, indicated schematically by arrows 72, cold fluid is applied through the tube and ejects through the nozzles. Consequently, the portion of the stent which heats up is only the front portion which then expands (FIG. 6b). By moving the tube backwards, the remaining parts of the stent may thus be gradually expanded.

Figure 7A:
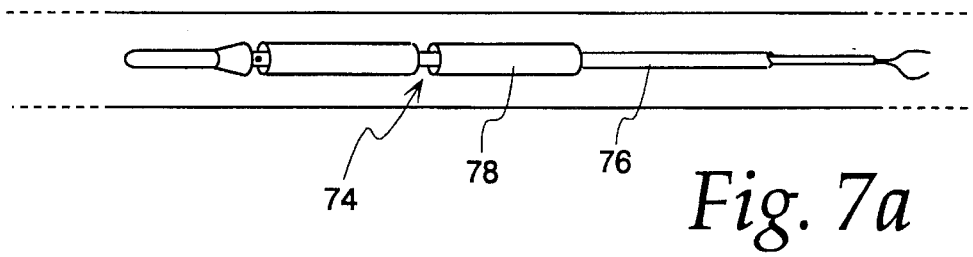
FIG. 7 depicts a stent in accordance with another embodiment of the invention.
Figure 7B:
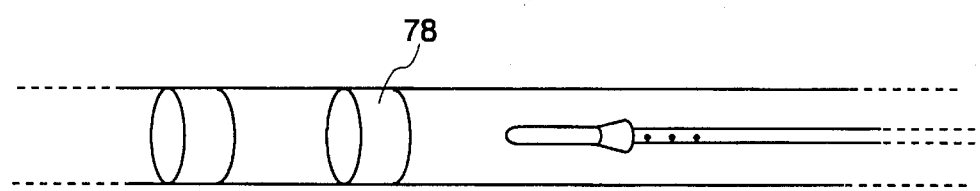

Attention is now being made to FIG. 7 showing another embodiment in accordance with the invention. In this embodiment, a cylindrical stent 74 is used as an alternative to a spiral stent of the embodiments of FIGS. 1–5. Other than this difference, the deployment of such a stent as well as the catheter device 76 used therefor are in essence similar to those of the previous embodiments. In its soft state (FIG. 7a) the stent 74 has a narrow diameter and each of its individual members 78 is relatively elongated. When heated (FIG. 7b), the stent expands and shortens and becomes deployed in the tubular organ. It will no doubt be appreciated by the artisan, that the super elasticity properties of a stent in accordance with this embodiment are less pronounced than in the case of stents having the form of a helical coil, as already pointed out above.

Figure 8:
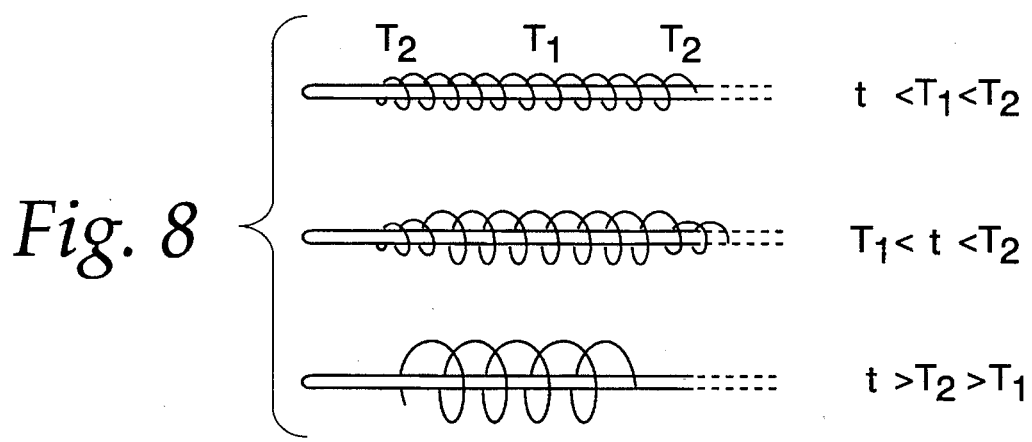
FIG. 8 and FIG. 9 depict stents having different transition temperatures throughout their length.

In order to allow for a very rapid opening of the stent, it may at times be possible to insert it into a position in a meta stable state as shown in FIG. 8. In order to achieve same, the stent is suitably made to have different transition temperatures at various regions throughout its length: the middle portion of the stent is made to have a transition temperature $T_i$ for changing from a soft to a super-elastic state being somewhat less than body temperature, e.g. 30°–36° C., and the extreme ends of the stent are made to have a higher transition temperature $T_2$, e.g. about 40°–80° C. The stent, in its soft state ($t<T_i<T_2$), is coiled tightly around a catheter and then inserted into the desired tubular organ. Owing to the body heat ($T_i<t<T_2$), the middle portion of the stent changes into its super-elastic state, but owing to the anchoring forces of the extreme ends of the stent, it does not expand and in fact is in an unequilibrium meta stable state. When the stent is heated by one of the above described means, to a temperature above the transition temperature of the two extreme ends ($t>T_2>T_1$), it immediately and very rapidly expands to the diameter it has in the super-elastic state.

Figure 9:
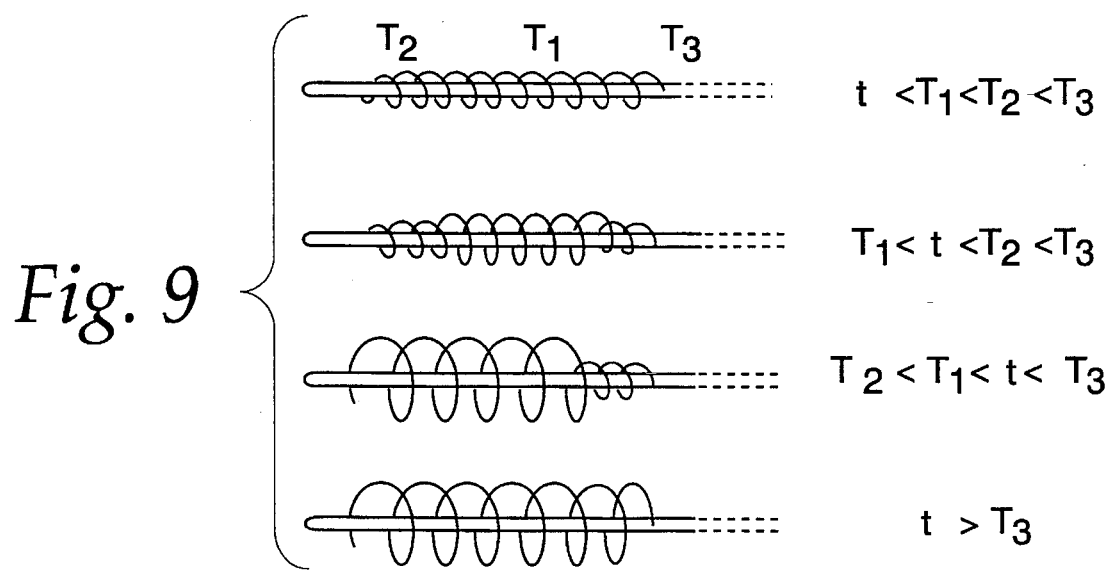

When the stent expands, it also shrinks in length, as already pointed out above. Where the stent is placed in a constricted region of a tubular organ in order to widen this region, the stent is positioned inside this region and when it expands, the extra friction forces between the stent and the surrounding tissue at the constricted region, versus the lower forces in other regions, bring about that the stent will remain during expansion in this region of the tubular organ. Where however the stent is intended to be deployed at a specific point of a tubular organ having the same diameter throughout its length, e.g. in a coronary artery after catheterization, in order to ensure that the stent will not be displaced from its desired position, e.g. the region of catheterization, the principle of having different transition temperatures at various regions throughout the stent's length may be used. In such a case, shown in FIG. 9, the stent may be made to have three different transition temperatures throughout its length: a first transition temperature, $T_1$, which is lower than the body temperature at a middle portion; a second transition temperature, $T_2$, above body temperature at one end; and a third transition temperature, $T_3$, which is higher than $T_2$ at the other extreme end of the stent. When the stent is inserted into the tubular organ, it enters into its meta stable state similarly as above. The stent is then positioned so that the second end, the one having the transition temperature $T_3$, is in its correct position. The stent is then heated to a temperature above $T_2$ but less than $T_3$ and consequently the stent widens and shrinks in length towards the second end which still remains anchored on the catheter device. The stent may then be heated to a temperature above $T_3$ where the second end also expands and consequently the stent becomes fully deployed.

It is clear that by controlling the position of the end of the stent with the higher transition temperature, the position of the stent inside the tubular organ may be managed.

In order to reduce friction forces, it may at times be desired to coat the band or the wire constituting the stent with a hydrophilic coating which reduces its friction coefficient.

Figure 10:
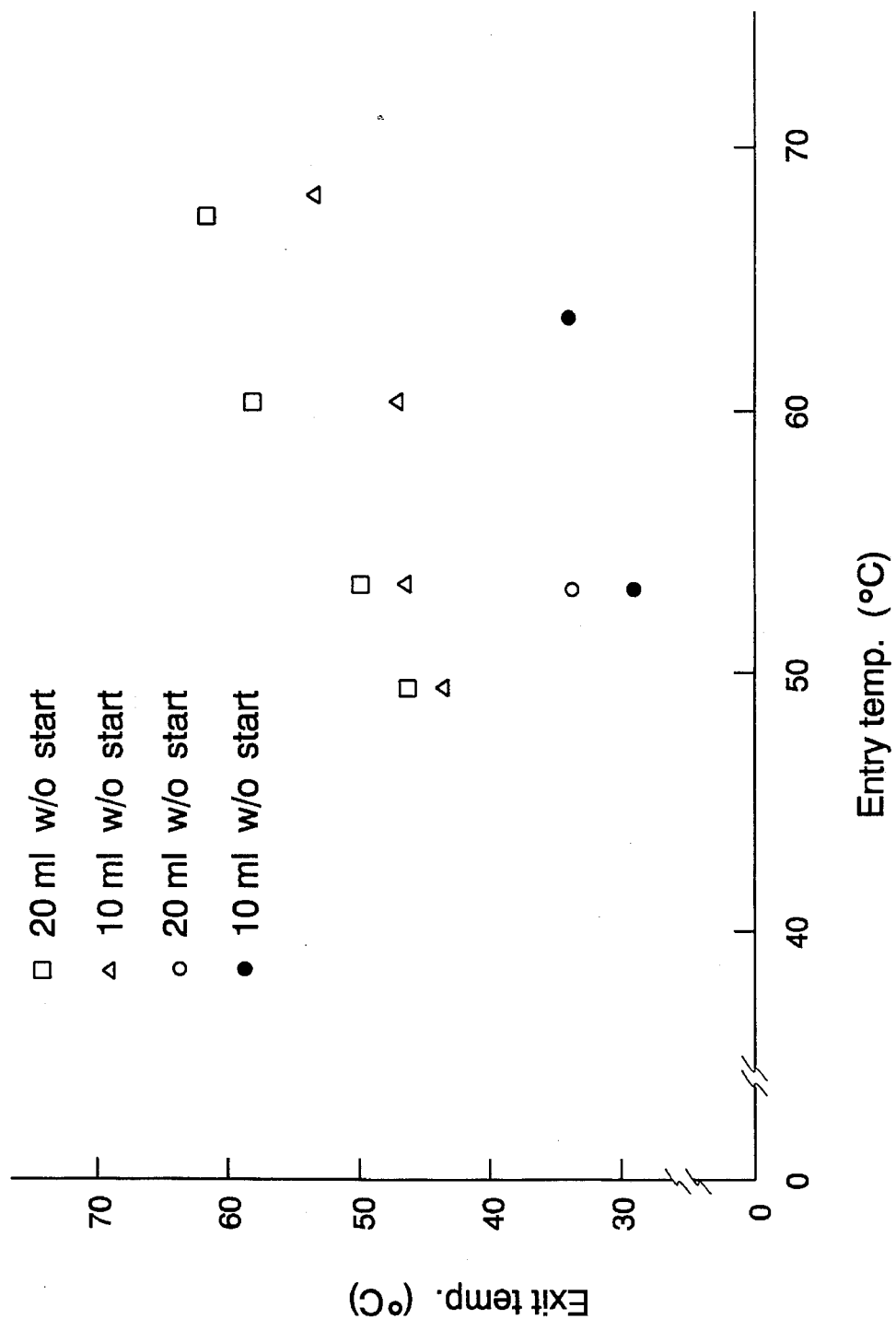
FIG. 10 depicts the results of a simulation experiment, in which reduction of liquid temperature by a stent of the invention during its expansion was measured.

Attention is now directed to FIG. 10 showing the results of an experiment in which water temperature after passing through a tube of 1 cm diameter was measured in several cases. In one experiment, 10 ml or 20 ml of water samples of various temperatures were passed through the tube. In another experiment, 10 ml and 20 ml samples of water were passed through the same tube but having inside the tube a stent in its soft state, which upon contact with the water expanded to its super-elastic state. The entry temperature of water and the exit temperature thereof were measured in each case and the results of the latter as the function of the former are shown in FIG. 8. As can be seen, while there was only a very small reduction in temperature where the tube did not contain a stent, there was a very marked decrease in temperature, e.g. to 33° C. after passing of 10 ml water having an entry temperature of 63° C. This great reduction in temperature results from the very high heat utilization by the stent during its expansion, and it shows that there is practically no risk in the ejection of warm fluids into tubular organs in order to cause expansion of the inventive stent.

We claim:

1. A stent for placing in a portion of a tubular organ so as to support the walls of the tubular organ in said portion such that the tubular organ in said portion will have a diameter above a critical diameter, the stent comprising:

a spiral coil or cylinder made of a two-way shape memory alloy; having a super-elastic scale in which the stent has a first diameter which is at least about the critical diameter but within a physiological range tolerated by said organ; and having a soft state in which the stent has a second diameter, after changing to this state from the super-elastic scale, which is less than said critical diameter;

the shape memory alloy has two transition temperatures being within a range that will not damage biological tissue, of which a first transition temperature, being a temperature which is above body temperature, is a temperature in which said alloy changes from said soft state to said super-elastic state and of which a second transition temperature, being a temperature which is below body temperature, is a temperature in which said alloy changes from said super-elastic state to said soft state, so that after changing into one of the two states, the stent remains in that state at body temperature.

2. A stent according to claim 1, being a helical coil.

3. A stent according to claim 1, being a member of two or more discrete stent members, that are placed one next to another along said portion of a tubular organ.

4. A stent according to claim 1, having two end portions and a middle portion, the middle portion having a first set of a first and second transition temperature, and at least one of the end portions has a second set of a first and a second transition temperature, at least one of the transition temperatures in the second set is different from a corresponding transition temperature in the first set.

5. A catheter device for deploying a stent in a tubular organ, such that the stent will support walls of the tubular organ to secure that the tubular organ will have a critical diameter above a critical diameter comprising a catheter tube or rod carrying a stent coiled on an end segment of the tube or rod, the stent comprising:

a spiral coil or cylinder made of a two-way shape memory alloy; having a super-elastic state in which the stent has a first diameter which is at least about the critical diameter but within a physiological range tolerated by said organ; and having a soft state in which the stent has a second diameter, after changing to this state from the super-elastic state, which is less than said critical diameter;

the shape memory alloy has two transition temperatures being within a range that will not damage biological tissue, of which a first transition temperature, being a temperature which is above body temperature, is a temperature in which said alloy changes from said soft state to said super-elastic state and of which a second transition temperature, being a temperature which is below body temperature, is a temperature in which said alloy changes from said super-elastic state to said sort state, so that after changing into one of the two states, the stent remains in that state at body temperature;

the stent carried on the catheter tube or rod in said soft state.

6. A device according to claim 5, comprising means for removal of a stent deployed in a tubular organ.

7. A device according to claim 5, comprising an elongated flexible duct having a guide member at a front end with a base of a diameter larger than the flexible duct, and having an annular member fitted on said tube at a distance from said guide member; the duct having a closed front end and being fitted at its front end portion, proximal to said guide member, with lateral fluid ejection nozzles; the stent in its said soft state being held on said duct on the portion thereof being between said guide member and said annular member; upon insertion of the device into a portion of a tubular organ, warm fluid is ejected through said nozzles, whereby the stent, changing into its super-elastic state, expands and is deployed in said portion.

8. A device according to claim 7, wherein said annular member can slide over said duct, the device further comprising a tube enveloping said duct which upon rearward movement of the duct during deployment of the stent, arrests the rearward movement of said annular member which in turn arrests the rearward movement of the stent.

9. A device according to claim 5, carrying a helical stent and comprising an elongated flexible rod containing within it two electrical wires leading to electrical terminals at the front, stent carrying portion of said rod, said terminals being in contact with two ends of the helical stent whereby electric current can pass through the stent which causes heating of the stent and brings to its transition from the soft state to the super-elastic state, whereby it expands, and after expanding the contact between said terminals and said stent are released.

10. A device according to claim 9, comprising a tube with an open front end having a diameter so that it can accommodate said rod with a stent carried on its terminal segment, the tube and the rod being moveable relative to one another so that said terminal segment can be pushed forward out of the front end of the tube.

11. A device according to claim 5, comprising a flexible elongated rod containing an electrical lead connected to an RF source and terminating at its front end at an RF antenna located within the terminal, stent carrying segment of said rod.

* * * * *

UNITED STATES PATENT AND TRADEMARK OFFICE
CERTIFICATE OF CORRECTION

PATENT NO. : 5,562,641
DATED : October 8, 1996
INVENTOR(S) : Flomenblit et al.

It is certified that error appears in the above-indentified patent and that said Letters Patent is hereby corrected as shown below:

At column 7, line 31, change "scale" to --state--.

At column 7, line 37, change "scale" to --state--.

At column 8, line 17, change "sort" to --soft--.

Signed and Sealed this

Twenty-second Day of July, 1997

Attest:

BRUCE LEHMAN

Attesting Officer     Commissioner of Patents and Trademarks